US006872411B1

(12) United States Patent
Ross et al.

(10) Patent No.: US 6,872,411 B1
(45) Date of Patent: Mar. 29, 2005

(54) PROCESS FOR THE MANUFACTURE OF PROBIOTIC CHEESE

(75) Inventors: Reynolds Paul Ross, Kilworth (IE); Gerald Francis Fitzgerald, Midleton (IE); John Kevin Collins, Doughcloyne (IE); Gerald Christopher O'Sullivan, Ballinveltig (IE); Catherine Gerardine Stanton, Kilworth (IE)

(73) Assignees: Enterprise Ireland, Dublin (IE); Teagasc, The Agriculture and Food Development Authority, Dublin (IE)

( * ) Notice: Subject to any disclaimer, the term of this patent is extended or adjusted under 35 U.S.C. 154(b) by 0 days.

(21) Appl. No.: 09/701,358
(22) PCT Filed: May 26, 1999
(86) PCT No.: PCT/IE99/00047
§ 371 (c)(1),
(2), (4) Date: Dec. 18, 2000
(87) PCT Pub. No.: WO99/62348
PCT Pub. Date: Dec. 9, 1999

(51) Int. Cl.$^7$ .............................. A23C 9/12; C12N 1/20
(52) U.S. Cl. ............................ 426/36; 426/34; 426/38; 426/43; 426/580; 426/582; 435/252.9
(58) Field of Search ........................... 426/34, 36, 580, 426/582, 38, 39, 40, 42, 43; 435/252.9, 853

(56) References Cited

PUBLICATIONS

Collins et al., Selection of Probiotic Strains for Human Application, International Dairy Journal, vol. 8, 1998, 487–490.*
Lee et al., Journal of Food Science, vol. 55, No. 2, 1990, pp. 386–390.*
Lee et al., Journal of Food Science, vol. 55, No. 2, 1990, pp. 391–397.*
Lynch et al., International Dairy Journal, 6(1996), pp. 851–867.*
Broome et al., Australian Journal of Dairy Technology, 45, Nov., 1990, No. 2, pp. 67–73.*
Gormes et al., Netherlands Milk & Dairy Journal, vol. 49 (1995) pp. 71–95.
Dinakar et al., J. Dairy Sci., vol. 77 (1994) pp. 2854–2864.
T. Klaenhammer: "Probiotic cheese" Internatiional Dairy Journal, vol. 8, No. 5/6, 1998, pp. 491–496, XP002116067 p. 491–p. 493; figure 2.
Database FSTA Online! International Food Information Service (IFIS), Franfurt/Main, DE AN=1999–00–p1445, C. Stanton: "Probiotic Cheese"XP002115138 abstract & International Dairy Journal, vol. 8, No. 5/6, 1998, pp. 491–496, This paper is from a Symposium held in Cork on Sep. 30 to Oct. 2, 1997.

C. Lynch: "Manufacture of Cheddar Cheese with and Without adjunct Lactobacilli under controlled microbiological conditions" International Dairy Journal, vol. 6, No. 8, 1966, pp. 851–867, XP002115824 p. 851; figures 1,6; table 3 p. 856.
Gomez M J et al: "Debittering Acitivity of Peptidases from Selected Lactobacilli Strains in Model Cheese" Milchwissenschaft, vol. 51, No. 6, Jan. 1, 1996, pp. 315–319, XP000624592 ISSN: 0026–3788 p. 316; table 4.
Lee B H et al: "Influence of Homofermentative Lactobacilli on the Microflora and Soluble Nitrogen Components in Chedder Cheese" Journal of Food Science, vol. 55, No. 2, Mar. 1, 1990, pp. 391–397, XP000126289 ISSN: 0022–1147 p. 391–p. 392; figures 1–4.
Lee B H et al: "Influence of Homofermentative Lactobacilli on Physicochemical and Sensory Properties of Cheddar Cheese" Journal of Food Science, vol. 55, No. 2, Mar. 1, 1990, pp. 386–390, XP000126288 ISSN: 0022–1147 p. 386, column 2 –p. 387, column 1; table 1.
R. Hargrove: "New type of ripened low–fat cheese" Journal of Dairy Science, vol. 49, No. 7, 1996, pp. 796–799, XP002115136 Chapaign, Illinois US p. 797.
Broome M C et al: "The Use of Non–Starter Lactobacilli I Cheddar Cheese Manufacture" Australian Journal of Dairy Technology, vol. 45, No. 2, Nov. 1, 1990, pp. 6773, XP000166076 ISSN: 0004–9433 p. 67, column 2—p. 68, column 1.
E. Tuomola: "Addition of Some Probiotic and Dairy Lactobacillus Strains to CACO–2 Cell Cultures" International Journal of Food Mircobiology vol. 41, No. 1, 1998, pp. 4551, XP002115137 p. 45 –p. 46; table 1.
Fox P F et al: Significance of Non–Starter Lactic Acid Bacteria in Cheddar Cheese: Australian Journal of Dairy Technology, vol. 53, No. 2, Jun. 1, 1998, pp. 83–89, XP000772490 ISSN: 0004–9433 Lb. Paracasei = formerly Lb. Casei subsp. Pseudoplantarum. p. 83, column 2.

* cited by examiner

Primary Examiner—Leslie Wong
(74) Attorney, Agent, or Firm—Birch, Stewart, Kolasch & Birch, LLP

(57) ABSTRACT

A process for the manufacture of a probiotic cheese, such as Cheddar cheese, comprises adding a 0.0–5.5% inoculum of a strain of *Lactobacillus paracasei*, which is non-pathogenic, acid and bile tolerant and adherent to human epithelial cells, as a starter adjunct to cheese milk, said *L. paracasei* strain being capable of growing during the ripening phase to a level of $10^7$ cfu/g or greater. The *L. paracasei* strains are found to grow and proliferate to high cell numbers (in excess of $10^8$ cfu/g) in the cheese over eight months of ripening, even when added at a relatively low inoculum. The presence of the *L. paracasei* strains is found to have negligible effects on cheese composition, flavor and aroma.

14 Claims, 9 Drawing Sheets

PROCESS FOR THE MANUFACTURE OF PROBIOTIC CHEESE

This application is the national phase under 35 U.S.C. §371 of PCT International Application No. PCT/IE99/00047 which has an International filing date of May 26, 1999, which designated the United States of America.

TECHNICAL FIELD

This invention relates to the manufacture of probiotic cheese and, in particular, to the manufacture of a probiotic cheese which contains at the time of consumption a viable, actively growing strain of an added bacterium.

BACKGROUND ART

The importance of probiotic-containing products to maintenance of health and well-being is becoming a key factor affecting consumer choice, resulting in rapid growth and expansion of the market for such products, in addition to increased commercial interest in exploiting their proposed health attributes. The majority of probiotic foods already on the market, such as fermented milks and yoghurt are fresh products and are generally consumed within days or weeks of manufacture. In contrast, hard cheeses, such as Cheddar have long ripening times of up to two years.

Probiotic bacteria are described as 'living' microorganisms, which upon ingestion in certain numbers exert health benefits beyond inherent basic nutrition. Probiotics may be consumed either as a food component or as a non-food preparation. Foods containing such bacteria fall within the 'functional foods' category and these are described as 'foods claimed to have a positive effect on health'. Such products are gaining more widespread popularity and acceptance throughout the developed world and are already well accepted in Japan and the USA. Furthermore, increased commercial interest in exploiting the proposed health attributes of probiotics has contributed in a significant way to the rapid growth and expansion of this sector of the market.

The potential health-promoting effects of dairy products which incorporate probiotic organisms such as Lactobacillus and Bifidobacterium spp. has stimulated a major research effort in recent years. To date, the most popular food delivery systems for these cultures have been freshly fermented dairy foods, such as yoghurts and fermented milks, as well as unfermented milks with cultures added.

There are relatively few reports concerning cheese as a carrier of probiotic organisms, even though there are a small number of 'probiotic cheeses' currently on the market.

In 1994, Dinakar and Mistry (J. Dairy Sci. 77:2854–2864) incorporated *Bifidobacterium bifidum* into Cheddar cheese as a starter adjunct. This strain survived well in the cheese and retained a viability of approximately $2 \times 10^7$ cfu/g even after 6 months of ripening, without adversely affecting cheese flavour, texture or appearance. This example suggested that Cheddar could provide a suitable environment for the maintenance of probiotic organisms at high levels over long time periods. However, no growth of the *B. bifidum* was observed in the cheese during the ripening period and thus it is important to emphasise that the Bifidobacterium strain did not grow during manufacture and/or ripening and thus had to be added at a relatively high inoculum. In another study, bifidobacteria were used in combination with *Lb. acidophilus* strain Ki as a starter in Gouda cheese manufacture (Gomes, A. M. P. et al. (1995); Neth. Milk Dairy J. 49:71–95). The two strains were used as sole starters, requiring relatively large inocula (3%) of both strains and adaptation of cheese making technology. In this case, there was a significant effect on cheese flavour in the resultant product after 9 weeks of ripening, possibly due to acetic acid production by the bifidobacteria.

In order to exert a probiotic effect, cultures must maintain their viability in food products through to the time of consumption, which for Cheddar cheese is many months after manufacture.

Cheese is a milk product in which the whey protein/casein ratio does not exceed that of milk and which is obtained by coagulation of milk by the action of rennet, followed by whey drainage. Starter cultures containing lactic acid bacteria are initially required during cheese making to metabolise lactose, thereby producing lactic acid and reducing the pH. During Cheddar cheese manufacture for example, the starter lactococci grow, reaching maximum levels of approximately $10^9$ to $10^{10}$ cfu/g at salting. Conditions in the cheese however, such as high salt in moisture (S/M), low pH, lack of a fermentable carbohydrate and low temperature of ripening can result in a dramatic decline in starter numbers during the early weeks of ripening. The rate of decline depends on a number of characteristics of the strain, including autolytic properties, salt tolerance and phage resistance. In the meantime, a population of non-pathogenic organisms, referred to as non-starter-lactic acid bacteria (NSLAB), chiefly composed of lactobacilli (*Lb. plantarum, casei* and *brevis*) and pediococci (*Pediococcus pentosaceus*) proliferate as the cheese ripens, a process that is generally performed at 2–16° C. It is believed that NSLAB gain access tothe cheesemilk during the manufacturing stage or that they survive pasteurisation in an attenuated state. Regardless, their numbers increase rapidly reaching maximum levels of $10^7$ to $10^8$ cfu/g in ripened Cheddar cheese. Indeed, in mature cheese, NSLAB may represent the principal flora. Their role in determining cheese quality remains unclear. NSLAB are generally enumerated using an aerobic plate count on Rogosa or Lactobacillus Selective (LBS) agar.

It may not be cost-effective to add probiotic strains to cheese in amounts corresponding to that finally required for a probiotic product at time of consumption. Rather what is required is a probiotic strain which can be added as a starter adjunct at a low inoculum to cheese and which grows to the required values of $\sim > 10^7$ cfu/g.

What is required, therefore, for a probiotic cheese with a long ripening time such as Cheddar is a probiotic strain which can survive and grow throughout manufacture and the ripening period.

DISCLOSURE OF INVENTION

The invention provides a process for the manufacture of a probiotic cheese, which process comprises adding a 0.05–0.5% inoculum of a strain of *Lactobacillus paracasei* isolated from the human gastrointestinal tract, which is non-pathogenic, acid and bile tolerant and adherent to human epithelial cells, as a starter adjunct to cheese milk, said *L. paracasei* strain being capable of growing during the ripening phase to a level of $10^7$ cfu/g or greater.

We have found that said strain of *L. paracasei* has the ability to survive the cheese manufacturing process and the capacity to grow and survive during the ripening/storage period. The strain of *L. paracasei* used in the process according to the invention also has the ability to survive passage through the gastrointestinal tract as hereinafter demonstrated. The presence of the added *L. paracasei* strain has been found to have negligible effects on cheese composition, flavour and aroma.

Preferably, a 0.1–0.25% inoculum of the *L. paracasei* is added to the cheese milk.

Also, preferably the ripening phase is at least six months.

Further, preferably, the ripening phase is eight months or greater.

The *L. paracasei* strains used in the process according to the invention have been found to grow and proliferate to high cell numbers in cheese over eight months of ripening, when added at a low inoculum as described herein.

Thus, in one embodiment of the invention, the *L. paracasei* is capable of growing during the ripening phase to a level of $10^8$ cfu/g or greater.

Preferably, the *L. paracasei* is tolerant to temperatures of 37° C. or greater.

Also, preferably the *L. paracasei* can be enumerated and distinguished from the resident flora.

Most preferably, the added *L. paracasei* cells are enumerated and distinguished by a randomly amplified polymorphic DNA (RAPD) method which allows the generation of discrete DNA fingerprints for the respective strains.

The RAPD used allowed the generation of discrete DNA fingerprints for each strain which were clearly distinguishable from those generated by the natural flora of the cheeses.

Preferably, the cheese manufactured is a hard cheese.

In an especially preferred embodiment the cheese is Cheddar cheese.

Cheddar cheese has particular advantages as a carrier of a probiotic micro-organism as described herein. Having a higher pH than the more traditional probiotic foods (e.g. yoghurts and fermented milks), it provides a more stable milieu to support their long-term survival. Furthermore, the matrix of the cheese and its relatively high fat content offers protection to probiotic bacteria during passage through the gastrointestinal tract (GIT).

The *L. paracasei* strains used in accordance with the invention were obtained from University College Cork, under a restricted Materials Transfer Agreement, together with a number of other strains for the purposes of investigation as described in the Examples.

The *L. paracasei* strains were found to have the requisite properties for use in cheese manufacture whereas, for example, the *Lactobacillus salivarius* strains investigated died during the ripening period.

The *L. paracasei* strains used herein have the requisite ability to influence the microflora of both the cheese and the GIT, the ability of the culture to grow in dairy-based media, such as whey and phage inhibitory media and the ability of the culture to survive and/or grow during manufacture and throughout the shelf-life of the cheese product.

The invention also provides *Lactobacillus paracasei* strain NFBC 338.

Also the invention provides *Lactobacillus paracasei* strain NFBC 364.

Samples of these bacteria have been deposited at The National Collections of Industrial and Marine Bacteria Limited (NCIMB) on May 29, 1998 and have been accorded the accession numbers NCIMB 40954 and NCIMB 40955, respectively.

In a fiber embodiment of the invention there is provided a probiotic cheese ready for consumption which contains a viable, actively growing strain of *L. paracasei* as hereinbefore defined in an amount of $10^7$ cfu/g or greater, following manufacture thereof using said *L. paracasei* as a starter adjunct.

An especially preferred cheese is Cheddar cheese.

Probiotic Cheddar cheeses can be manufactured in accordance with the invention containing high levels of *L. paracasei* strains ($10^8$ cfu/g cheese) at a relatively low cost to the producer and using identical manufacturing procedures. Importantly, we have shown that incorporation of these strains does not impact negatively on cheese quality, including aroma, flavour and texture. In addition, our results suggest that cheese also compares very favourably with yoghurt regarding delivery of viable cells to the GIT despite the apparent age difference of the products.

MODES FOR CARRYING OUT THE INVENTION

Figure 1A:
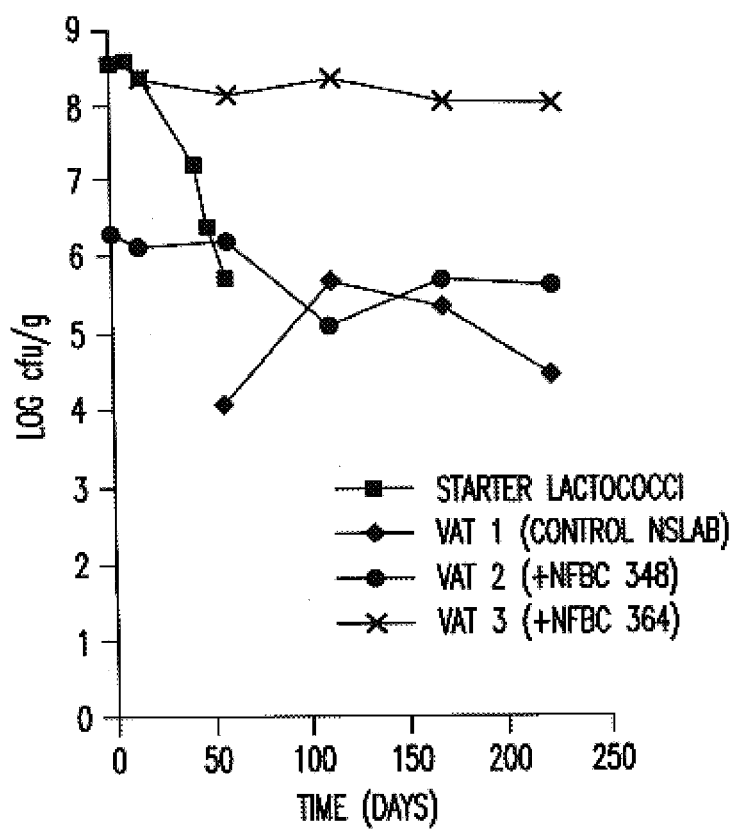
FIG. 1A is a graph of log cfu/g versus time (days) representing survival of lactobacilli and starter during cheese ripening in Trial 1 as described in Example 2.

The invention will be further illustrated by the following examples:

EXAMPLE 1

Probiotic Strain Identification/enumeration

A pre-requisite to the successful enumeration of added probiotic strains is to be capable of selectively identifying these from the natural, often complex microflora found in food products. Since NSLAB can reach levels of up to $10^7$–$10^8$ cfu/g in cheese during ripening it was necessary to evaluate a number of methods aimed at selectively enumerating the lactobacilli added as starter adjuncts from these NSLAB.

The probiotic Lactobacillus strains used in this Example had previously been isolated from the human gastrointestinal tract, and were obtained from Prof. J. K. Collins, Microbiology Dept., University College Cork, Ireland under the aforementioned Materials Transfer Agreement. These strains were identified as *L. salivarius* (ssp. *salivarius*) and *L. paracasei* (ssp. *paracasei*) by SDS-PAGE analysis of total cell protein. (Reuter, G. (1990) Bifidobacteria microflora 9:107–118) and were designated *Lb. salivarius* NFBC 310, NFBC 321 and NFBC 348 and *L. paracasi* NFBC 338 and NFBC 364. NSLAB Lactobacillus strains (*Lb. curvatus* DPC 2042 and 2081, *L. plantarum* DPC 2102 and 2142 and *L. casei* ssp. *casei* DPC 2047 and 2103) which had previously been isolated from 8 week old commercial Cheddar cheeses, were obtained from the culture collection of the Dairy Products Research Centre. All Lactobacillus strains were routinely cultured in MRS broth (Dinakar, P. and V. V. Mistry (1994)) (Difco Laboratories, Detroit, Mich., USA) under anaerobic conditions (anaerobic jars with 'Anaerocult A' gas packs; Merck, Darmstadt, Germany) at 30° C. and 37° C. for NSLAB and probiotic strains, respectively. Solid media were prepared by adding 1.5% agar to broth medium. Stock cultures were maintained at −80° C. in 40% glycerol-supplemented MRS broth. Each culture was sub-cultured twice in MRS broth before use from stock. *Lactococcus lactis* ssp. *cremoris* strains 227 and 223, obtained from Chr. Hansen's Laboratories (Little Island, Cork, Ireland) in the form of freeze-dried pellets, were used as starters for cheese-making. These were grown overnight at 21° C. in heat-treated (90° C. for 30 min) 10% (w/v) reconstituted skim-milk (RSM).

Bacteriological Analyses of Cheeses

Viability of lactobacilli (both probiotic adjuncts and NSLAB) in the inoculated cheese-milk and in the cheeses during ripening was determined on LBS agar after 5 days of anaerobic incubation at 30° C. while starter lactococci were enumerated on LM17 agar after 3 days incubation at 30° C. Coliforms were enumerated in cheese-milk and cheeses on Violet Red Bile Agar (VRBA; Oxoid) at 37° C. for 24 hours. Cheeses were aseptically sampled in duplicate for bacteriological analysis, at intervals during ripening. Cheese samples were emulsified in sterile 2% (w/v) trisodium citrate, diluted in maximum recovery diluent and appropriate dilutions pour-plated. After 1, 3 and 6 monthly intervals, 20 individual Lactobacillus colonies from each cheese were randomly selected from the LBS agar plates for RAPD-PCR analysis.

a) Bile and Temperature Tolerance of Lactobacillus Adjuncts

To investigate the tolerance of both the probiotic and NSLAB Lactobacillus isolates to bile, overnight MRS broth cultures of each of the Lactobacillus strains were serially diluted in maximum recovery diluent (Oxoid Ltd, Basingstoke, Hampshire, UK) and appropriate dilutions pour-plated on MRS agar with 0, 0.1, 0.3, 0.5, 1.0 or 3.0% porcine bile (Sigma Chemical Co., Poole, Dorset, England). After 3 days incubation, the plates were examined and where colonies were present, their numbers and sizes were recorded. Temperature tolerance of the probiotic lactobacilli was investigated by pour-plating appropriate dilutions of overnight cultures on LBS agar (Rogosa, M. et al. (1951) J. Baterial 62:132–133) (Becton Dickinson, Cockeysville, Md., USA) and incubating the plates anaerobically both at 37° C. (which is the optimum temperature of growth for these strains) and at 42° C. Colony numbers obtained after 5 days were compared. In the same way, the temperature tolerance of these strains and NSLAB, following isolation from Cheddar cheese was also investigated.

The bile and temperature tolerance of both the human-derived lactobacilli and a selection of NSLAB was first determined in the hope that either of these parameters could form a basis for the selection of the adjunct from the product. Both the probiotic adjuncts and NSLAB Lactobacillus strains varied considerably with regard to their bile tolerance. Two of the NSLAB isolates used in this Example were tolerant to levels of porcine bile of up to 3% compared to the lactobacilli added as starter adjuncts, which were inhibited at 0.3% bile. Therefore selections based on bile tolerance would not be useful in distinguishing the probiotic adjunct lactobacilli incorporated into Cheddar cheese in this Example from the NSLAB lactobacilli. Similarly, temperature tolerance could not be used as a basis for selection of the probiotic lactobacilli from NSLAB. NSLAB isolated from Irish Cheddar cheeses do not grow at 45° C. while some of the human-derived probiotic lactobacilli may withstand such temperatures (Kandler, O. and Weiss, N. (1989) In P. H. A. Sneath (ed.), Bergey's manual of determinative bacteriology, Vol. 2. The Williams & Wilkins Co., Baltimore, Md.). A temperature of 42° C. was evaluated for selective enumeration of the probiotic strains from the NSLAB. While the probiotic Lactobacillus strains, isolated from fresh cultures or Cheddar cheese early in ripening were capable of growth at 42° C., they failed to grow at this temperature when isolated from mature cheese. Furthermore, some NSLAB lactobacilli were found to be capable of growth at 42° C., confirming that this procedure was non-selective for the human-derived probiotic Lactobacillus strains from Cheddar cheese.

b) RAPD-PCR Analysis

RAPD-PCR analysis was carried out on each of the probiotic Lactobacillus strains and on cultures grown from Lactobacillus colonies isolated from Cheddar cheese. Genomic DNA was isolated from 1.5 ml of overnight MRS broth cultures using a modification of the method of Hoffman and Winston (Hoffman, C. S., and Winston, F. (1997) Gene 57:267–272). This procedure utilises shearing with glass beads to lyse the cells, and was modified as outlined by Coakley et al. (Coakley, M. et al. (1996); J. Inst. Brew. 102:344–354). One microliter of the extracted DNA was used in subsequent PCR amplifications, which were performed in a total volume of 25 $\mu$l in a Perkin-Elmer (Norwalk, Conn., USA) DNA Thermal Cycler. The method employed was essentially as described by Coakley et al. ((1996) supra ) and used a single primer of arbitrary nucleotide sequence (5' ATGTAACGCC 3'), obtained from Pharmacia Biotech, (Uppsala, Sweden). DNA was amplified for 35 cycles using the following temperature profile: denaturing at 93° C. for 1 min, annealing at 36° C. for 1 min followed by polymerisation at 72° C. for 1 min. Taq DNA polymerase (0.625 Units, Bioline) was added to the reaction mix during the first denaturation step (Hot Start).

Between 5 and 10 $\mu$l of the PCR reaction was analysed on a 1.5% (w/v) agarose (Sigma) gel with ethidium bromide staining. A 100 bp ladder (Pharmacia) was used as a molecular weight standard. Gels were run for approximately 3 hours at 100 V and the DNA visualised by UV transillumination.

Consequently, the Randomly Amplified Polymorphic DNA (RAPD) method, which involves PCR using an arbitrary primer, was used to generate DNA fingerprints for each of the probiotic strains. Each of the Lactobacillus strains generated reproducible discrete DNA fingerprints, which were found to be substantially different from those of representative NSLAB lactobacilli. Thus, the RAPD method proved to be a successful means of identifying the probiotic strains and demonstrated potential as a means of selective identification of the strains from the NSLAB flora in Cheddar cheese.

EXAMPLE 2
Incorporation of Lactobacillus Species into Cheddar Cheese

Laboratory-scale cheesemaking trials (Trials 1 and 2) were performed initially using 25 L of pasteurised whole milk in each cheese vat. To limit contamination with wild lactobacilli, these cheeses were manufactured under controlled bacteriological conditions, as described by McSweeney, P. et al. ((1994); Irish J. Agric. Food Res. 33:183–192). A 1.5% inoculum of the mixed-strain starter culture was used and in each trial one vat (Vat 1) acted as a control to which starter only was added. To each of the experimental vats, one probiotic Lactobacillus strain, grown overnight in 10% RSM, was added as an adjunct to the starter culture. In Trial 1, the probiotic adjuncts L. salivarius NFBC 348 and L. paracasei NFBC 364 were added at an inoculum level of 0.1% to Vats 2 and 3, respectively. In the second trial, L. salivarius NFBC 310 (Vat 2), L. salivarius NFBC 321 (Vat 3) and L. paracasei NFBC 338 (Vat 4) were inoculated at a level of 0.2%. Cheddar cheeses were then manufactured according to standard procedures as follows: Filter-sterilised rennet (Chr. Hansen's Laboratories) was added at a concentration of 0.07 ml/liter 35 min after starter and adjunct addition, and the curd was cut approximately 40 min later. Curds were cooked to 39° C., pitched at pH 6.1 and milled at approximately pH 5.3. Salt was added at a rate of 2.8% (w/w) and the curds were placed in moulds and pressed at approximately 200 kPa overnight. The cheeses were removed from the moulds, vacuum-packed and ripened at 8° C. for approximately 8.5 months. Subsequently two pilot-scale cheesemaking trials (Trials 3 and 4) were performed using two of the adjunct Lactobacillus strains which were found to maintain high viability in the laboratory-scale cheeses during ripening. In each trial, two vats, one experimental and one control, each containing 450 liters of standardised (fat:protein=1) pasteurised whole milk were used. As in the laboratory-scale trials, a 1.5% inoculum of the starters 223 and 227 was added to each vat. In addition, in each trial the experimental vat (Vat 2) contained a 0.1% inoculum of either L. paracasei NFBC 364 (Trial 3) or NFBC 338 (Trial 4) added as a starter adjunct. The cheesemaking procedure was as previously described for the laboratory-scale cheeses except that the salting level was 2.7% and the curds were pressed overnight at approximately 413 kPa.

Figure 2A:
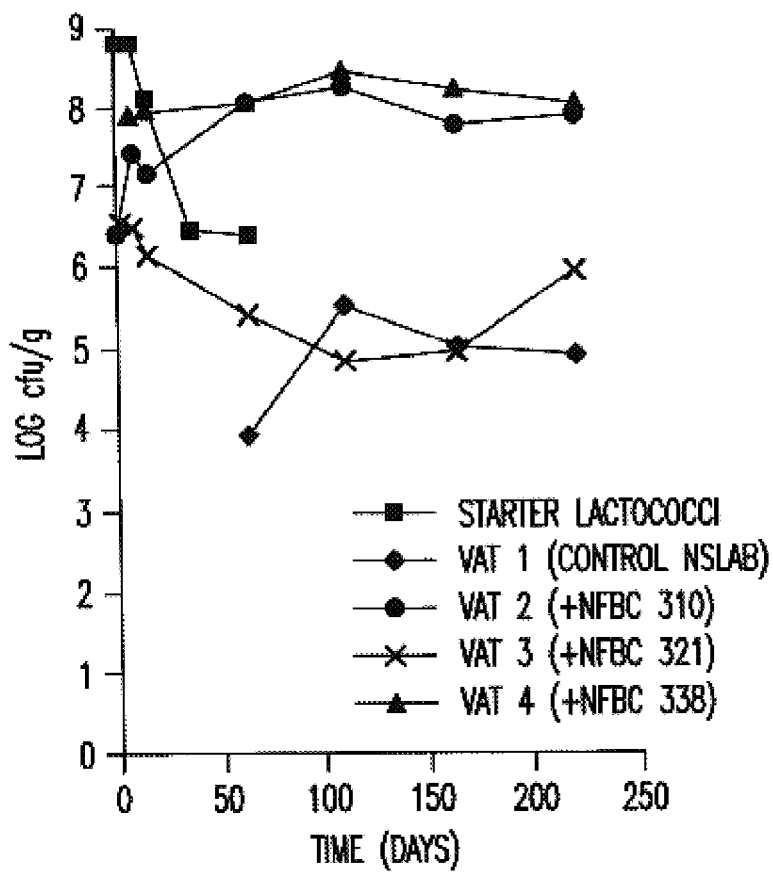
FIG. 2A is a graph of log cfu/g versus time (days) representing survival of lactobacilli and starter during cheese ripening in Trial 2 as described in Example 2.

Initially, laboratory-scale cheese trials were performed under microbiologically controlled conditions (thus limiting development of high numbers of NSLAB during ripening) to assess the performance of five probiotic Lactobacillus strains in Cheddar cheese. Firstly, for inoculation purposes, the performance of these strains in RSM was investigated. None of the strains performed well in milk (levels of only $10^7$–$10^8$ cfu/ml achieved) and were subsequently found to be non- or only weakly proteolytic (data not shown). Thus, using a 0.1–0.2% inoculum of these L. salivarius and paracasei strains as starter adjuncts, relatively low levels of $10^4$–$10^5$ cfu/ml milk were obtained in the experimental vats during cheese manufacture as shown in Table 1. All adjunct lactobacilli were found to survive the cheese manufacturing process and, given their poor growth in milk and the low inoculum used, were shown to have no effect on acid production during the process (data not shown). Results demonstrate that cheese made with NFBC 364 and NFBC 338 L. paracasei adjuncts (Trial 1 Vat 3, Trial 2, Vat 4, respectively) contained high levels of these probiotic strains after 8 months of ripening; with final counts of $9.2 \times 10^7$ and $1.4 \times 10^8$ cfu/g achieved, respectively as shown in FIGS. 1A and 2A.

TABLE 1

Baterial counts (cfu/ml) in milk used for the manufacture of Cheddar cheese, after inoculation with adjunct and/or starter cultures

| Cheese inoculum[1] | Lactobacilli | Lactococci |
|---|---|---|
| Trial 1[3] | | |
| V1, 1.5% 227/223 | ND[2] | $3.2 \times 10^6$ |
| V2, 1.5% 227/223 + 0.1% L. salivarius NFBC 348 | $1.3 \times 10^5$ | $3 \times 10^6$ |
| V3, 1.5% 227/223 + 0.1% L. paracasei NFBC 364 | $2.4 \times 10^5$ | $2.9 \times 10^6$ |
| Trial 2[3] | | |
| V1, 1.5% 227/223 | ND | $2.7 \times 10^6$ |
| V2, 1.5% 227/223 + 0.2% L. salivarius NFBC 310 | $2.9 \times 10^5$ | $3.8 \times 10^6$ |
| V3, 1.5% 227/223 + 0.2% b. salivarius NFBC 321 | $2 \times 10^5$ | $2.8 \times 10^6$ |
| V4, 1.5% 227/223 + 0.2% L. paracasei NFBC 338 | $2.3 \times 10^4$ | $4.5 \times 10^5$ |
| Trial 3[4] | | |
| V1, 1.5% 227/223 | ND | $2.4 \times 10^6$ |
| V2, 1.5% 227/223 + 0.1% L. paracasei NFBC 338 | $1.7 \times 10^5$ | $4.1 \times 10^6$ |
| Trial 4[4] | | |
| V1, 1.5% 227/223 | ND | $3.10^5$ |
| V2, 1.5% 227/223 + 0.1% L. paracasei NFBC 364 | $8.9 \times 10^5$ | $1.1 \times 10^6$ |

Figure 1B:
FIGS. 1B–1D are RAPD PCR profiles of a representative number of Lactobacillus isolates from each of the cheeses as described in Example 2.
Figure 1C:
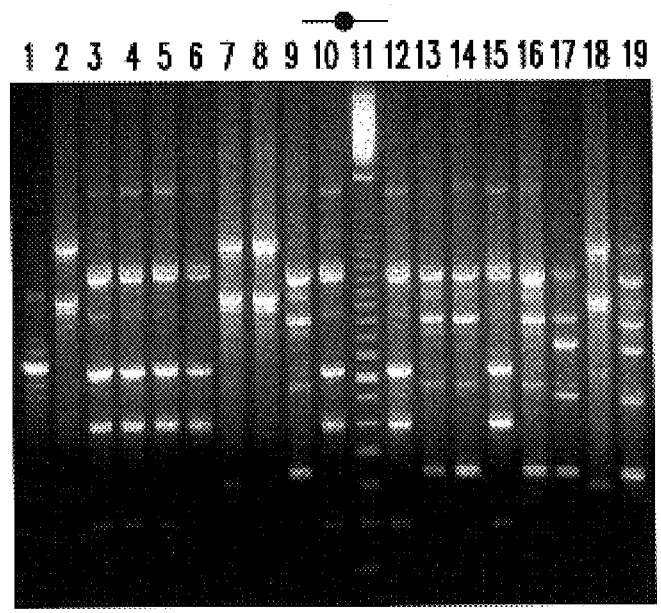
Figure 1D:

[1]227/223 = L. Lactis ssp. cremoris 227 + 223
[2]ND = Non-detectable
[3]Trial 1 and 2 cheeses manufactured at laboratory-scale under microbiologically controlled conditions
[4]Trial 3 and 4 cheeses manufactured at pilot-scale using the two Lactobacillus adjunct strains (NFBC 338 and NFBC 364) which showed good survival in the laboratory-scale cheeses during ripening FIGS. 1B–1D are RAPD PCR profiles of a representative number of Lactobacillus isolates from each of the cheeses (B, C and D); Lane 1 shows the RAPD profile of the probiotic Lactobacillus strain added to the cheese at manufacture, while a 100 bp ladder is shown at Lane 19 (B) and Lane 11 (C and D) and all other lanes (B, C and D) show RAPD profiles of Lactobacillus isolates from 6-month-ripened cheeses.

Figure 2B:
FIGS. 2B–2E are RAPD PCR profiles of a representative number of Lactobacillus isolates from each of the cheeses as described in Example 2.
Figure 2C:
Figure 2D:

FIGS. 2B–2D are RAPD PCR profiles of a representative number of Lactobacillus isolates from each of the cheeses (B, C, D and E); Lane 1 shows the RAPD profile of the probiotic Lactobacillus strain added to the cheese at manufacture, while a 100 bp ladder is shown in Lane 19 (B, C, D and E) and all other lanes (B, C, D, and E) show RAPD profiles of Lactobacillus isolates from 6-month-ripened cheeses.

Figure 2E:

The high levels of probiotic strains was confirmed following comparison of the RAPD PCR fingerprints generated for L. paracasei strains NFBC 364 and NFBC 338 (FIG. 1D and FIG. 2E, lane 1) and those obtained for lactobacilli isolated from the cheeses (FIG. 1D and FIG. 2E, lanes 2–10 and 12–20) which were found to be identical. In contrast, although lactobacilli grew to high levels ($1 \times 10^8$ cfu/g) in the cheese to which strain NFBC 310 was added (Trial 2 Vat 2), and subsequently remained at this level throughout ripening (FIG. 2A), these lactobacilli (FIG. 2C, lanes 2–10 and 12-2-) were identified by RAPD PCR as NSLAB. Levels of lactobacilli in cheeses with L. salivarius adjuncts NFBC 348 and NFBC 321 (Trial 1 Vat 2 and Trial 2 Vat 3, respectively) declined to $1.2 \times 10^5$ cfu/g and $8.6 \times 10^4$, respectively, after 4 months of ripening (FIGS. 1A and 2A), although these levels did increase slightly to reach final levels of $3.5 \times 10^5$ and $1.1 \times 10^6$ cfu/g, respectively after 8 months of ripening.

Interestingly, the genetic fingerprints of isolates taken from each of these cheeses after 6 months revealed that these lactobacilli were predominantly NSLAB (FIG. 1C and FIG. 2D, respectively). Thus, the *L. salivarius* strains used in this Example did not maintain viability in Cheddar cheeses during ripening. Furthermore, many of the NSLAB isolated from these cheeses in which the adjunct strains declined (FIG. 1C, lanes 3–6 and FIG. 3D, lanes 12–18) and from the control cheeses to which no probiotic adjuncts were added (FIG. 1B, lanes 9–13 and FIG. 2B, lanes 3–9) yielded identical PCR-generated DNA fingerprints. This suggests that the DNA was obtained from identical strains and shows a predominance of certain Lactobacillus strains in the NSLAB population of these cheeses.

Figure 3A:
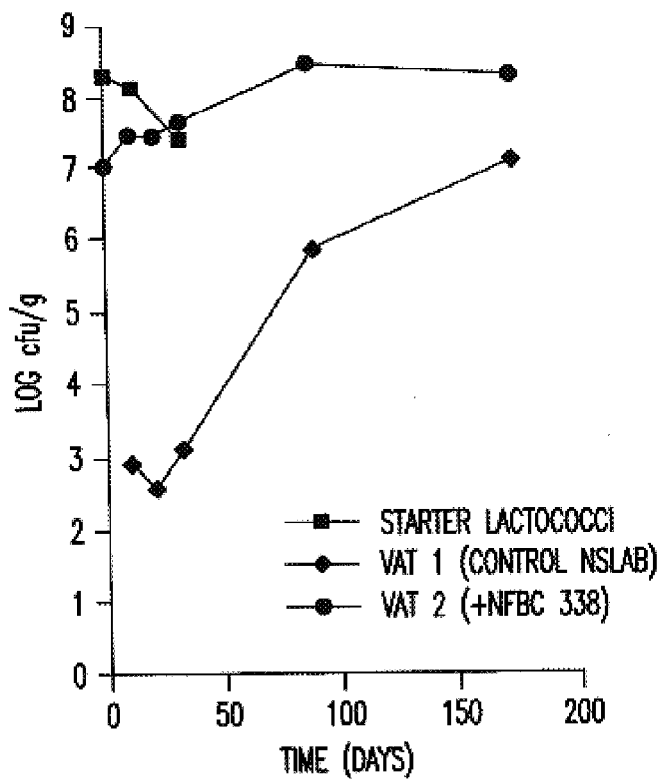
FIG. 3A is a graph of log cfu/g versus time (days) representing survival of Lactobacilli and starter during cheese ripening in Trial 3 as described in Example 2.
Figure 3B:
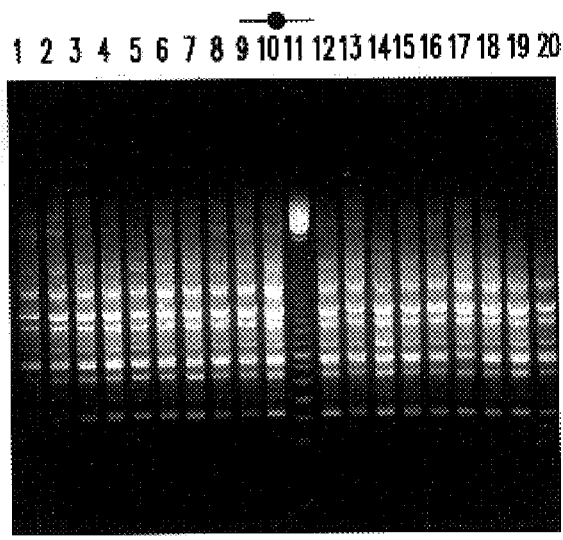
FIG. 3B depicts RAPD PCR profiles of a representative number of Lactobacillus isolates from Vat 2 cheese as described in Example 2.
Figure 4A:
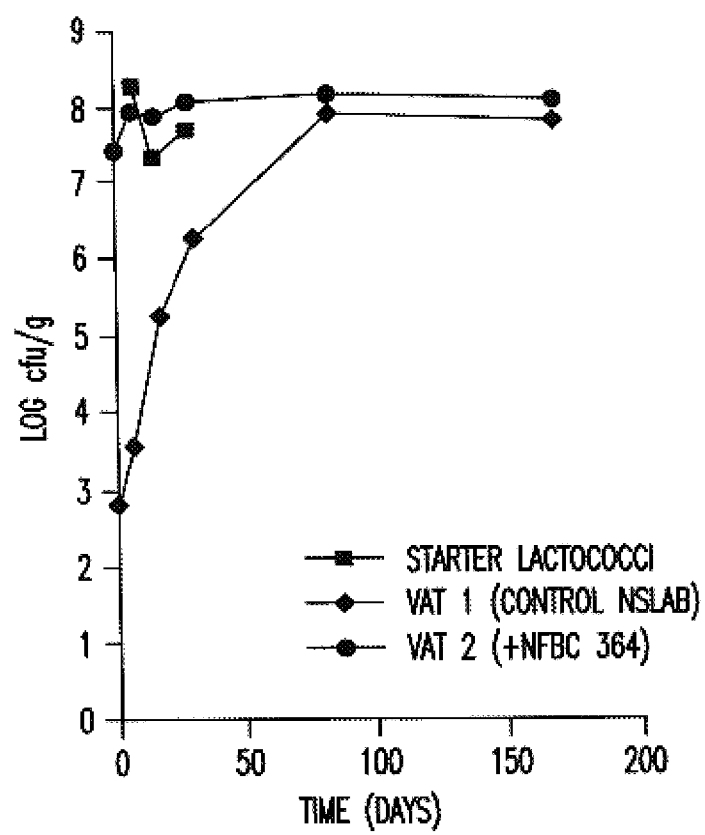
FIG. 4A is a graph of log cfu/g versus time (days) representing survival of Lactobacilli and starter during cheese ripening in Trial 4 as described in Example 2.
Figure 4B:
FIG. 4B depicts RAPD PCR profiles of a representative number of Lactobacillus isolates from Vat 2 cheese as described in Example 2

Subsequently, pilot-scale cheese trials were performed, where only the two *L. paracasei* strains, NFBC 338 and NFBC 364, which survived to high levels in the laboratory-scale trials were incorporated into Cheddar cheese. These strains were added to Trial 3 Vat 2 (NFBC 338) and Trial 4 Vat 2 (NFBC 364) at inocula of 1.7 and $8.9 \times 10^5$ cfu/ml cheese-milk, respectively as shown in Table, 1. Thereafter, both NFBC 338 and NFBC 364 grew in the cheese from initial numbers of $1.1 \times 10^7$ and $2.7 \times 10^7$ cfu/g, respectively, to reach levels of between 1.5 and $2.9 \times 10^8$ cfu/g after 3 months of ripening and viability was sustained at this level for the remainder of the ripening period (FIGS. 3A and 4A). As in the laboratory-scale cheeses, these results were confirmed by RAPD PCR analysis (as described in Example 1) of a number of isolates from each of these cheeses (FIGS. 3B and 4B).

Taken together, the data from the laboratory- and pilot-scale cheese trials provide molecular-based evidence for the persistence in Cheddar cheese of strains selected for their potential as probiotics. In order to appreciate the beneficial effects of 'probiotic' foods, it has been proposed as indicated above, that viable probictic organisms should be present at levels of at least $10^7$ viable cells per gram or milliliter of product. The probiotic-containing cheeses obtained in accordance with the invention contained levels of up to $10^8$ cfu/g cheese, thus satisfying the criteria for a 'probiotic' food product.

It should also be noted that lactococcal starter numbers in the control cheeses of all trials showed a typical decline during the ripening period (FIGS. 1A, 2A, 3A and 4A). However, due to the growth of lactobacilli on the LM17 medium used to enumerate, these starter organisms, it was possible only to monitor starter in these cheeses, to which no adjunct lactobacilli had been added, and then only in the early stages of ripening.

RAPD PCR analysis, when used as an identification method, was capable of determining that probiotic *L. paracasei* strains grew and maintained high viability ($10^8$ cfu/g) in cheese, while the particular *L. salivarius* adjunct strains used did not appear to be suited for such an application. Furthermore, survival of these probiotic Lactobacillus strains at high numbers in Cheddar cheese was achieved using a relatively low inoculum (0.1–0.2%) in the cheese vat and without altering the cheesemaking process in any way. This was possible because these strains were added as starter adjuncts and were not therefore necessary for acid production during cheese-making. Thus, the process according to the invention for incorporation of probiotic organisms into Cheddar cheese offers certain advantages to industry; no alteration of existing cheese-making technology and low cost due to the low inoculum required.

EXAMPLE 3
Cheese Compositional Analysis

Grated cheese samples were analysed in duplicate for salt by a potentiometric method (Irish Dairy Federation (1979); Cheese and processed cheese. Determination of chloride content: potentiometric titration method. IDF Standard 88), fat by the Gerber method (Irish Standard (1955); Determination of the percentage fat in cheese. Irish Standard. 69), moisture by oven-drying at 102° C. (Irish Dairy Federation (1982); Determination of the total solids content (cheese and processed cheese). IDF Standard 4A) and protein on a LECO FP-428 nitrogen determinator. The pH of a slurry, prepared by blending 12 ml $H_2O$ with 20 g grated cheese, was measured using a standard pH meter (Radiometer, Copenhagen, Denmark).

The composition of the cheese was generally found to be within the range typical for Cheddar as shown in Table 2.

TABLE 2

Composition[1] of control and probiotic Cheddar cheeses

| Cheese trial | Moisture | Salt | S/M[2] (%) | Fat | Protein | pH |
|---|---|---|---|---|---|---|
| Trial 1 | | | | | | |
| V1 | 38.28 | 1.53 | 4.0 | 31.5 | 26.33 | 5.4 |
| V2 | 38.24 | 1.70 | 4.45 | 32.0 | 26.63 | 5.2 |
| V3 | 39.89 | 1.23 | 3.08 | 31.0 | 25.79 | 5.3 |
| Trial 2 | | | | | | |
| V1 | 37.48 | 1.64 | 4.38 | 33.0 | 26.5 | 5.2 |
| V2 | 35.73 | 1.81 | 5.07 | 33.0 | 26.99 | 5.1 |
| V3 | 37.22 | 1.61 | 4.33 | 33.0 | 27.27 | 5.1 |
| V4 | 38.01 | 1.71 | 4.55 | 33.0 | 27.27 | 5.1 |
| Trial 3 | | | | | | |
| V1 | 35.61 | 1.76 | 4.94 | 33 | 26.33 | 5.2 |
| V2 | 36.74 | 1.72 | 4.68 | 33 | 26.56 | 5.2 |
| Trial 4 | | | | | | |
| V1 | 34.88 | 2.05 | 5.88 | 34.5 | 26.17 | 5.4 |
| V2 | 35.14 | 1.80 | 5.12 | 35.0 | 26.42 | 5.3 |

[1]Means of duplicate analyses
[2]Salt-in-moisture

Some atypical values for salt-in-moisture (Vat 3), fat (all vats) and pH (Vat 1) were obtained for the Trial 1 cheeses which reflects the difficulty in controlling the cheesemaking parameters (i.e. temperature) at a laboratory-scale. In contrast, all the compositional analysis values obtained for the pilot-scale trials were generally within the typical range for Cheddar. Thus, the comparable values observed for control and experimental cheeses (Table 2) indicate that incorporation of probiotic lactobacilli as starter adjuncts, and their survival at high numbers, had no direct effect on cheese composition.

EXAMPLE 4
Sensory Evaluation of Cheddar Cheese

Cheeses were graded blindly after 3 and 6 months ripening by a commercial grader from a local cheese manufacturing plant. The cheeses were graded for flavour/aroma and body/texture, with maximum scores of 45 and 40, respectively. Minimum scores of 38 and 31 for flavour/aroma and body/texture, respectively are required for commercial Cheddar cheese. With the exception of the control cheese of Trial 2, all cheeses could be described as commercial grade with respect to sensory criteria, after 6 months of ripening, having achieved minimum scores of 38 and 31 for flavour/aroma and body/texture, respectively as shown in Table 3.

TABLE 3

Sensory evaluation of Cheddar cheeses at 6 months

| Cheese | Flavour/aroma[1] | Body/texture[2] |
|---|---|---|
| Trial 1 | | |
| V1 | 38 | 33 |
| V2 | 38 | 33 |
| V3 | 39 | 32 |
| Trial 2 | | |
| V1 | 37 | 33 |
| V2 | 39 | 32 |
| V3 | 38 | 33 |
| V4 | 38 | 32 |
| Trial 3 | | |
| V1 | 38 | 33 |
| V2 | 38 | 33 |
| Trial 4 | | |
| V1 | 39 | 33 |
| V2 | 38 | 33 |

[1]Maximum score = 45; minimum commerical score = 38
[2]Maximum score = 40; minimum commercial score = 31

Lactobacillus adjuncts have previously been reported to improve Cheddar cheese flavour (Broome, M. D., et al. (1990); Aust. J. Dairy Technol. 45:67–73) although, in some cases they were responsible for flavour defects (Puchades, R., et al. (1989); J. Food Sci. 54:885–888). In this Example, laboratory-scale cheeses with high levels of Lactobacillus adjuncts were found to have flavour and texture comparable to that of control cheeses, indicating that addition of these probiotic lactobacilli to Cheddar cheese had no adverse effects on sensory criteria. Furthermore, when repeated on a larger scale, sensory parameters remained unaffected by the presence of high levels of these adjuncts.

EXAMPLE 5

Proteolysis in Laboratory-scale Cheddar Cheeses

Cheeses were analysed by urea-PAGE (Shalabi, S. L., and Fox, P. F. (1987); Irish J. Food Sci. Technol. 11:135–151) using a Protean II xi vertical slab gel unit (Bio-Rad Laboratories, Ltd, Watford, Herts, UK) essentially with the stacking gel system of Andrews (Andrews, A. T. (1983); J. Dairy Res. 50:45–55). Cheese samples were prepared by dispersing 10 mg of grated cheese in 1 ml of sample buffer and heating at 50° C. for 5 min. Samples were stored at −20° C. until use and 10 μl was applied to the gel. Sodium caseinate (5 μl) was used as a standard for comparative purposes. Samples were electrophoresed at 280 V through the stacking gel and at 300 V through the resolving gel. Gels were stained with Coomassie Brilliant Blue G250 using the direct-staining procedure of Blakesley and Boezi (Blakesley, R. W., and J. A. Boezi (1977); Anal. Biochem 82:582–581).

Water-soluble extracts (pH 4.6) of each of the cheeses were prepared according to the method of Kuchroo and Fox (Kuchroo, C. N. and Fox, P. F.; (1982); Milchwissenshcaft 37:331–335) and freeze-dried. The size distribution of peptides in these freeze-dried extracts was determined by size-exclusion HPLC, using a TSK 2000 SW (Beckman Instruments Ltd, High Wickham, United Kingdom) gel permeation column (7.5 nm×60 cm) fitted to a Waters HPLC system (Waters Chromatography Division, Milford, Mass., USA). The column was eluted at a flow-rate of 1 ml/min with 30% acetonitrile containing 0.1% trifluoroacetic acid (TFA). The freeze-dried water-soluble extracts were reconstituted (3 mg/ml) in HPLC-grade water, filtered through a Whatman 0.2 μm filter and 20 μl applied to the column. Column eluates were continually monitored at 214 nm. Data were collected using a PC Minichrom system (VG Data Systems, Cheshire, United Kingdom) and results compared to a previously prepared calibration curve.

Individual free amino acids (FAA) in the water-soluble extracts were determined using a Beckman System 6300 High Performance Analyser (Beckman Instruments Ltd, High Wickham, United Kingdom) equipped with a Beckman P-N 338052 $Na^+$ column (12 cm×0.5 cm) as described by Lynch et al.(Lynch, C. M. et al. (1996); Int. Dairy J. 6:851–867). Chromatograms were collected using a computer-controlled Minichrom data processing package. Amino acid concentrations were expressed as μg/ml cheese extract which were subsequently converted to μg/gcheese.

Urea-PAGE electrophoresis patterns of whole cheese samples after 8 months of ripening (FIG. 5) are typical for Cheddar and do not show any differences in the extent of primary proteolysis between the control cheeses and those manufactured with adjunct lactobacilli.

Figure 5:
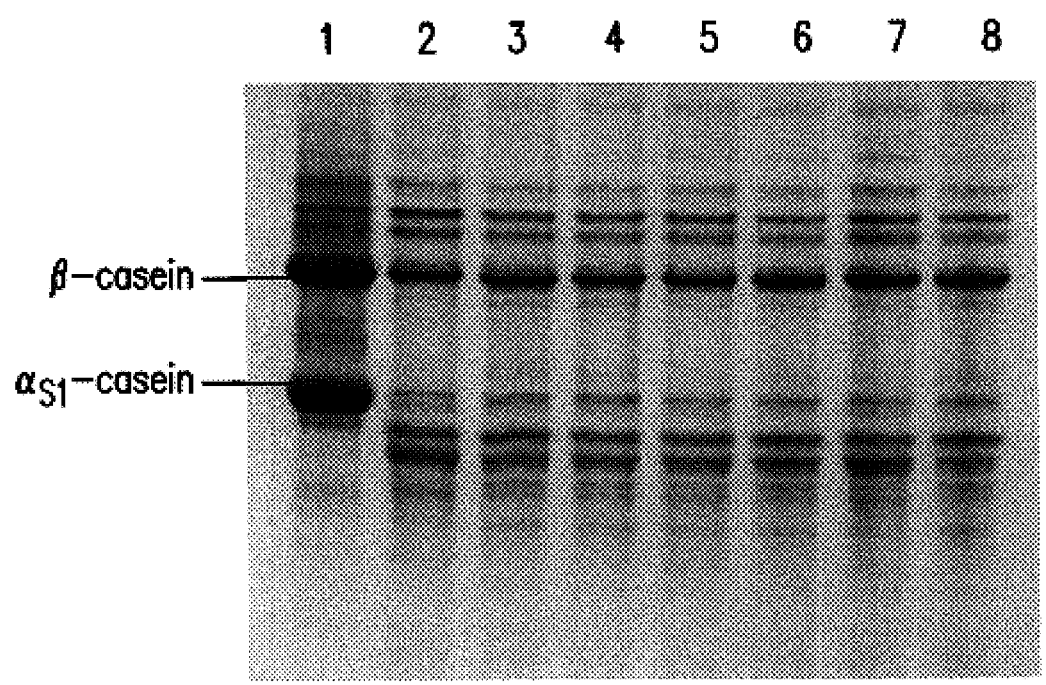
FIG. 5 is a urea PAGE of control and experimental Cheddar cheeses after eight months of ripening as described in Example 5.

FIG. 5 represents Urea-PAGE of control (Lanes 2 and 5) and experimental (Lanes 3, 4, 6, 7 and 8) Cheddar cheeses after 8 months of ripening. Lane 1 contains a sodium-caseinate standard.

The molecular weight distribution of peptides in water-soluble extracts from the cheeses (as measured by size-exclusion HPLC) serves as a further indication of the extent of proteolysis in the cheeses during ripening; the greater the extent of proteolysis, the higher the level of low molecular weight peptides generated. After 6 months of ripening, the levels of these low molecular weight peptides (<500 Da) were found to have accumulated to high levels in all cheeses (data not shown). Moreover, similar levels were detected in the control and experimental cheeses, even in those cheeses which had high levels of survival of adjunct lactobacilli (Trial 1 Vat 3, Trial, 2 Vat 4 cheeses), indicating that the extent of proteolysis in the cheeses as demonstrated by generation of small peptides, was not affected by adjunct addition. However higher levels of individual FAA were detected in the cheeses made with added lactobacilli, after 6 months of ripening (FIG. 6).

Figure 6A:
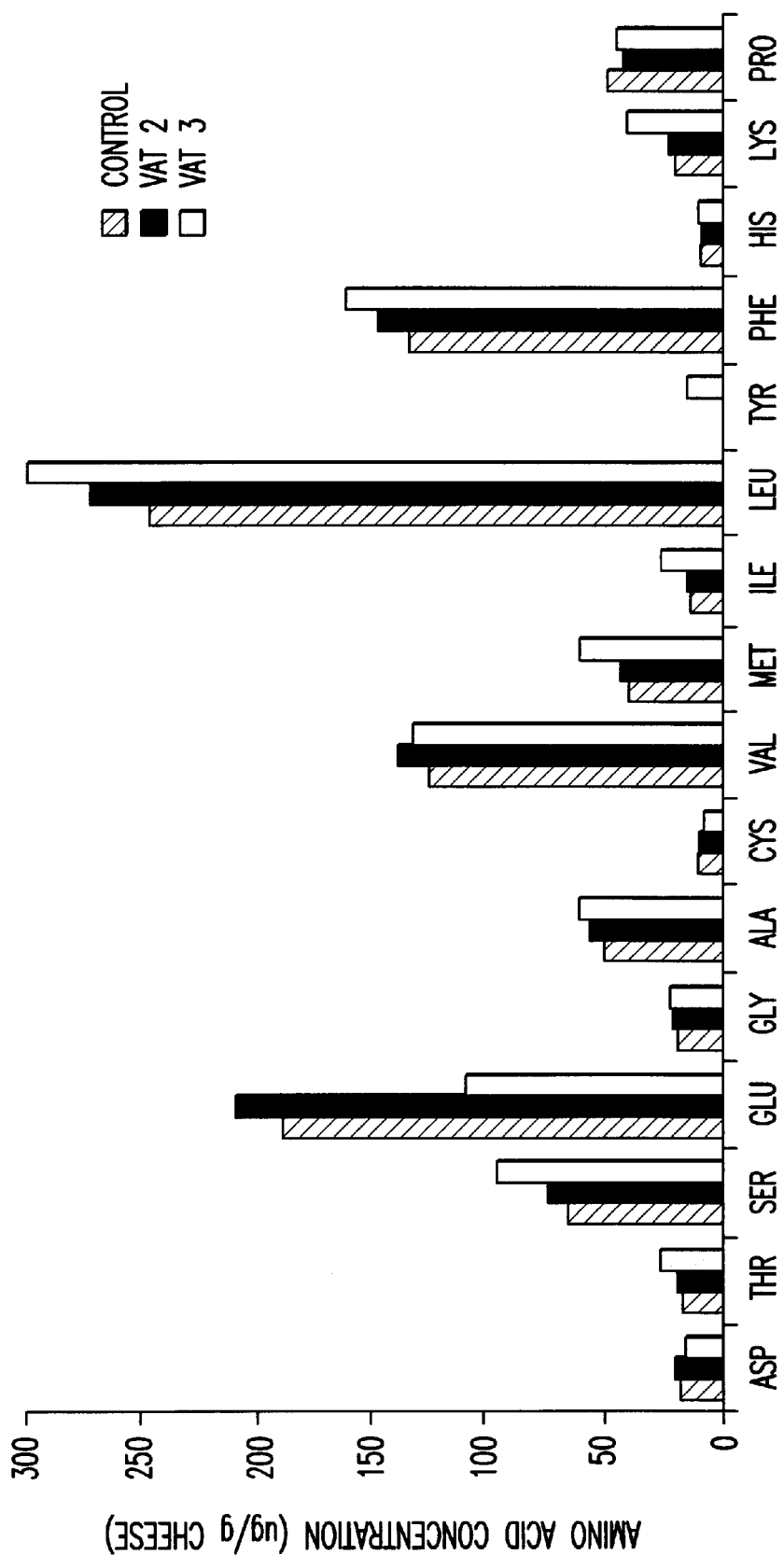
FIG. 6A shows the concentration of individual free amino acids in water-soluble extracts of six month old control and experimental cheeses found in Trial 1 as described in Example 5.
Figure 6B:
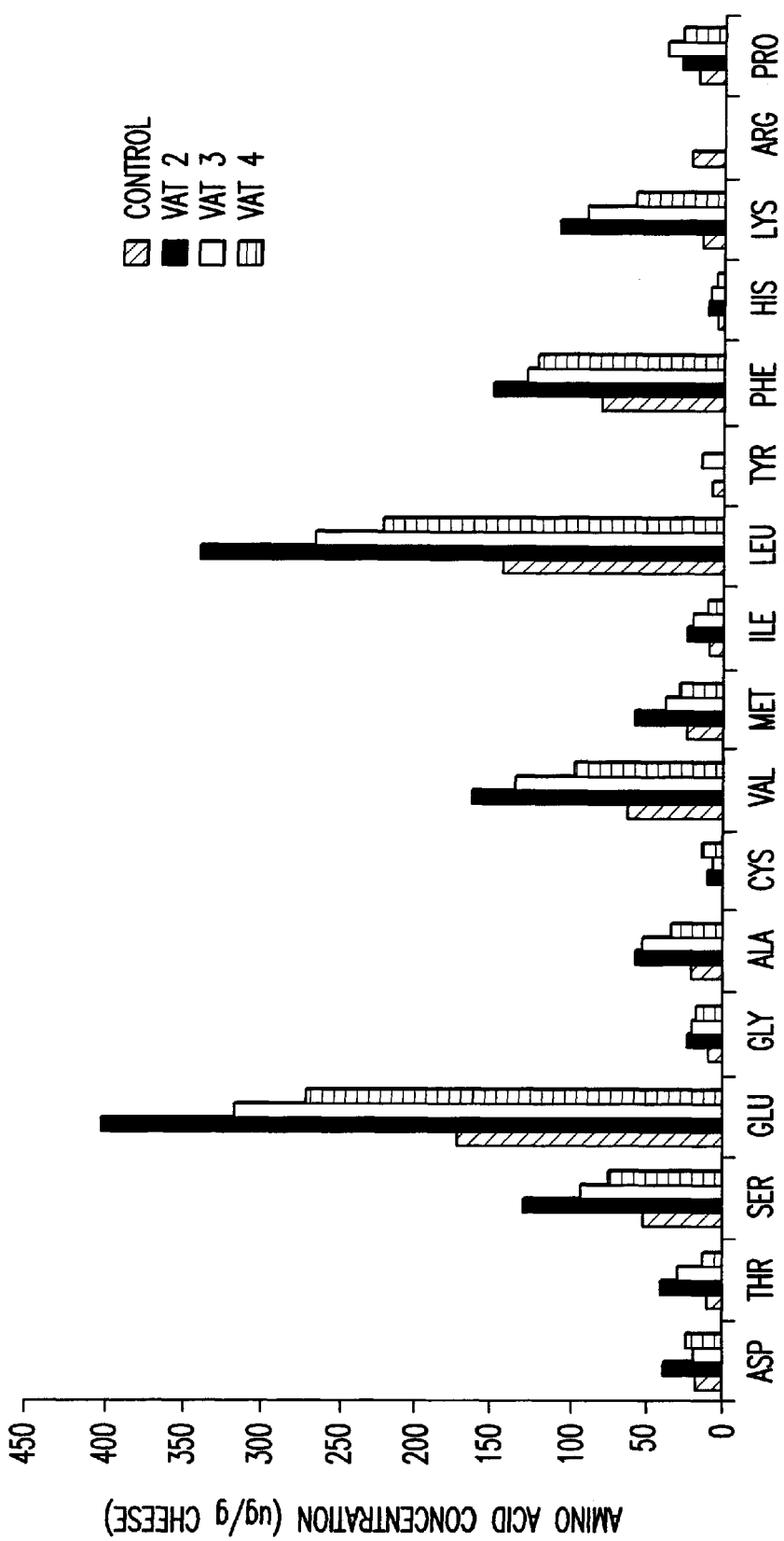
FIG. 6B shows the concentration of individual free amino acids in water-soluble extracts of six month old control and experimental cheeses found in Trial 2 as described in Example 5.

FIG. 6 depicts the concentration of individual free amino acids in water-soluble extracts of 6 month old control and experimental Cheddar cheeses of Trial 1 (A) and Trial 2 (B).

Most notably, concentrations of serine, methionine, leucine and phenlyalanine (Trial 1) in addition to glutamnic acid and valine (Trial 2) were higher in the cheeses made with added lactobacilli than in the control cheese to which no adjunct had been added (FIG. 6). This was found to be true even for the cheeses in which the Lactobacillus adjuncts declined during ripening. This may be accounted for by the release of intracellular peptidases as the organisms died and lysed. Thus, in general, the results suggest that the adjunct lactobacilli, whether they survived to high levels or not, did contribute to proteolysis in the cheese as demonstrated by increased formation of FAA.

The above results demonstrate that probiotic L. paracasei strains, incorporated into Cheddar cheese proved particularly suitable as starter adjuncts. These strains were found to grow and proliferate to high cell numbers in the cheese over 8 months of ripening, even when added at a relatively low inoculum. Furthermore, RAPD PCR proved extremely useful to distinguish these probiotic adjuncts from NSLAB. Moreover, the results from the control cheese suggest the predominance of certain NSLAB strains. While proteolysis during cheese ripening was influenced by the adjuncts at the level of FAA formation, cheese flavour, texture and appearance were not affected. Incorporation of these probiotic adjuncts into Cheddar cheese, as described herein can be achieved without alteration of the cheesemaking technology, thus making this system attractive for commercial exploitation. These results indicate that Cheddar cheese is an effective vehicle for delivery of these strains to the consumer with the attendant advantages.

We claim:

1. A process for the manufacture of a probiotic cheese, which process comprises adding a 0.05–0.5% vol/vol inoculum of a strain of *Lactobacillus paracasei*, which is non-pathogenic, acid and bile tolerant and adherent to human epithelial cells, as a starter adjunct to cheese milk, said *L. paracasei* strain being capable of growing during the ripening phase to a level of $10^7$ cfu/g or greater.

2. A process according to claim 1, wherein a 0.1–0.25% vol/vol inoculum of the *L. paracasei* is added to the cheese milk.

3. A process according to claim 1 or 2, wherein the ripening phase is at least six months.

4. A process according to claim 1, wherein the ripening phase is eight months or greater.

5. A process according to claim 1, wherein the *L. paracasei* is capable of growing during the ripening phase to a level of $10^8$ cfu/g or greater.

6. A process according to claim 1, wherein the *L. paracasei* is tolerant to temperatures of 37° C. or greater.

7. A process according to claim 1, wherein the *L. paracasei* can be enumerated and distinguished from the resident flora.

8. A process according to claim 7, wherein the added *L. paracasei* cells are enumerated and distinguished by a randomly amplified polymorphic DNA (RAPD) method which allows the generation of discrete DNA fingerprints for the respective strains.

9. A process according to claim 1, wherein the cheese manufactured is a hard cheese.

10. A process according to claim 9, wherein the cheese is Cheddar cheese.

11. *Lactobacillus paracasei* strain NFBC 338.

12. *Lactobacillus paracasei* strain NFBC 364.

13. A probiotic cheese ready for consumption which contains a viable, actively growing strain of *L. paracasei* as defined in claim 1 in an amount of $10^7$ cfu/g or greater, following manufacture thereof using said *L. paracasei* as a starter adjunct.

14. A probiotic cheese according to claim 13, which is Cheddar cheese.

* * * * *